United States Patent [19]
Maddox

[11] Patent Number: 5,212,060
[45] Date of Patent: May 18, 1993

[54] DRY TEST STRIP COMPRISING A DEXTRAN BARRIER FOR EXCLUDING ERYTHROCYTES

[75] Inventor: Catherine B. Maddox, St. Paul, Minn.

[73] Assignee: Genesis Labs, Inc., Edina, Minn.

[21] Appl. No.: 517,399

[22] Filed: Apr. 27, 1990

Related U.S. Application Data

[63] Continuation of Ser. No. 88,454, Feb. 25, 1987, abandoned.

[51] Int. Cl.$^5$ .................. G01N 33/53; G01N 21/00
[52] U.S. Cl. .................. 435/7.1; 422/56;
422/57; 435/4; 435/7.92; 435/7.93; 435/7.94;
435/7.95; 435/962; 435/970; 435/11; 435/14;
436/175; 436/529; 436/808; 436/825
[58] Field of Search ...... 422/56, 57; 435/4, 7.92-7.95,
435/970, 962, 11, 14, 805, 810; 436/529, 175,
808, 810, 825

[56] References Cited

U.S. PATENT DOCUMENTS

| | | | |
|---|---|---|---|
| 4,069,017 | 1/1978 | Wu et al. | 422/56 |
| 4,248,973 | 2/1981 | Kallies | 435/296 |
| 4,258,001 | 3/1981 | Pierce et al. | 422/56 |
| 4,446,232 | 5/1984 | Liotta | 422/56 X |
| 4,478,944 | 10/1984 | Gross et al. | 436/95 |
| 4,627,445 | 12/1986 | Garcia et al. | 128/770 |
| 4,637,403 | 9/1988 | Terminiello et al. | 436/530 |
| 4,678,757 | 7/1987 | Rapkin et al. | 436/169 |

FOREIGN PATENT DOCUMENTS

| | | | |
|---|---|---|---|
| 0097952 | 11/1984 | European Pat. Off. | 435/7 |
| 0141648 | 5/1985 | European Pat. Off. | 435/28 |
| 0143574 | 6/1985 | European Pat. Off. | 435/7 |
| 0130335 | 9/1985 | European Pat. Off. | 435/14 |
| 0207360 | 1/1987 | European Pat. Off. | 435/14 |

OTHER PUBLICATIONS

Kohler and Milstein, "Continuous Cultures of Fused Cells Secreting Antibody of Predetermined Specificity", *Nature*, vol. 256, pp. 495–497, Aug. 7, 1975.
Gantrez® S-95 *Polymer in Detergents*, published by GAF Corporation.
*Practical Immunology*, Hudson L. and Hay F. C. (1976), p. 17, Blackwell Scientific Publications, Oxford.
White et al., Principles of Biochemistry, 4th edition, pp. 50–51, (1968).
Pharmacia, Dextran Fractions-Dextran Sulfate-DEAE-Dextran, pp. 5–9, (1973).

*Primary Examiner*—Esther L. Kepplinger
*Assistant Examiner*—Carol A. Spiegel
*Attorney, Agent, or Firm*—Merchant, Gould Smith, Edell, Welter & Schmidt

[57] ABSTRACT

A dry test strip for the detection of an analyte in a test fluid is disclosed. The test strip comprises a porous detection zone containing a reactant system that can generate a signal in the presence of an analyte. The detection zone further comprises dextran as a barrier to prevent penetration of RBC's into the detection zone.

21 Claims, 2 Drawing Sheets

DRY TEST STRIP COMPRISING A DEXTRAN BARRIER FOR EXCLUDING ERYTHROCYTES

This is a continuation of application Ser. No. 07/018,454, filed Feb. 25, 1987, which was abandoned upon the filing thereof.

FIELD OF THE INVENTION

The invention relates to a dry test strip for an immunoassay or a chemical assay, useful in the detection of a clinically significant analyte in a biological or other test fluid containing red blood cells. Particularly the invention relates to a dry test strip having a barrier or exclusion layer that prevents interference in an analysis, in the detection or visualization of the signal produced by the analyte in a detection zone, by the presence of significant numbers of red blood cells.

BACKGROUND OF THE INVENTION

In recent years, dry test strips have been used to a considerable extent in the determination, especially in clinical chemistry and in the at-home monitoring, of blood levels of a variety of analytes including glucose. Dry test strips are typically manufactured in the form of a carrier strip having an absorbent layer impregnated with reagents that can detect and identify the presence of an analyte when contacted with a fluid containing the analyte. The presence of the analyte is typically signaled by color production, a color change or the production of a fluorescent or other electromagnetic radiation associated signal from a surface of the dry test strip. Since the accuracy, precision and rapidity of detection of the analyte can be dependent on an instrumental measurement or visual inspection of the dry test strip, any interference in measurement or inspection can reduce the value of the test.

We have found in the development of a variety of both immunoassays and chemical assays for detection of target analyte in test fluids having RBC such as whole blood, that a major cause of interference in the detection of a signal from an analyte detection zone arises from red blood cells (RBC) in the test fluid. As a test fluid containing significant numbers of red blood cells is contacted with an absorbent reagent zone layer on a carrier strip, the red blood cells along with the liquid and other components of the test fluid are absorbed into and penetrate through the absorbent layer and become intermingled in the detection zone. An RBC is known to comprise an outer membrane which contains a solution that is high in concentration of hemoglobin. The red blood cells and free hemoglobin that results from lysis of RBC can color the detection zone such that the zone can obtain a color that ranges from pink to a dark maroon. As a consequence, the production of a visual chemical signal can be wholly or partly obscured by the presence of the hemoglobin color in the detection zone. Further, the hemoglobin can block the production of electromagnetic radiation in a fluorescent-type signal generating indicator system. Both the rapidity of use, accuracy and precision of the dry test strip, the qualitative or quantitative analysis of analytes can be seriously inhibited by the presence of RBC in the detection zone or layer.

In the past, typical dry test strip devices used in the determination of analyte concentration in test fluids containing RBC have been wiped or washed after contacting the test fluid to remove excess RBC from the dry test strip. Wiping steps can reduce but cannot eliminate interference from the presence of RBC. Further, such wiping steps can introduce uncertainty into the application of a fixed volume of test fluid thus reducing the quantitative reliability of the analysis. In the past RBC interference was avoided by permitting freshly drawn blood samples to clot and centrifuging the clotted samples to separate RBC from serum. Such processing steps can introduce significant delays in obtaining analytical results. In certain instances with analyte targets that are chemically unstable or are rapidly metabolized such a delay can result in incorrect results.

Accordingly, a substantial need exists for a dry test strip that can exclude from the reagent zone red blood cells derived from a test fluid.

BRIEF DESCRIPTION OF THE INVENTION

The invention relates to a dry test device comprising an absorbent reagent zone and a barrier to red blood cell penetration through the reagent zone. The dry test device comprises an absorbent reagent zone containing a chemical assay or immunoassay that can generate a characteristic signal in the presence of an analyte target having a polysaccharide material that can limit the passage of RBC and hold the RBC on or near the surface of the absorbent reagent zone. Such a dry test strip can be used in a variety of formats. A dry test strip detection zone can be formed on a carrier strip to which a volume of blood can be applied for the purpose of determining the presence of the target analyte in the blood serum. Alternatively, a "pH-paper" type strip device can be used that can be unreeled from a strip dispenser. Another alternative is embodied in a mechanical device that combines a lance that can penetrate the skin to provide a blood sample, a wicking cloth that can contact the blood sample, and conduct the blood sample to the dry test strip device wherein the unique signal is produced with little or not RBC interference. Such devices can be visually read or can be read by instrumental methods and are disclosed in Garcia et al U.S. Pat. Nos. 4,637,403 and 4,627,445.

In operation in any of the test formats using the dry test devices of the invention, a test fluid is applied to the reagent zone directly or through a wick or other fluid application means, the test fluid penetrates the reagent zone but any RBC present are held by the polysaccharide trapping compound and cannot interfere with the visualization of the test signal typically on the side of the dry test device opposite the test fluid application site. The barrier layer can take the form of a separate layer covering the detection zone or can be a uniform dispersion of polysaccharide material throughout the detection zone. Visualization and rapid reaction of the reagent system can be aided by the presence of an aperture in the carrier test strip opposite the test fluid application site.

DETAILED DESCRIPTION OF THE INVENTION

In somewhat greater detail, the dry test strip immunoassay and chemical assay strips of the invention comprise an absorbent layer containing a reagent system that can generate a detectable signal in the presence of an analyte target. The reagent zone is protected from RBC interference in the visualization of a signal using a barrier composition comprising a polysaccharide material in a separate barrier layer or dispersed uniformly or non-uniformly throughout the detection zone.

The polysaccharide material used in the barrier layer of the dry test strip of the invention comprises a polymer containing repeating units of $C_5$ or $C_6$ monosaccharide compounds, or mixtures thereof. Such polymer chains can be made by linking the monosaccharides into branched and unbranched polysaccharide chains using a variety of linkages including alpha or beta (1→6), (1→5), (1→4), or other (2→6), (2→5), etc. linkages. Polysaccharides that can be used in the barrier layer of the invention come in a variety of forms and each form can be prepared in a variety of molecular weights. Specific examples of useful polysaccharides include starch and modified starch, cellulose and modified cellulose, aminopolysaccharides such as chitin or chitosan, and others.

A particularly preferred polysaccharide for use in the barrier layer of the dry test strip of the invention comprises dextran. Dextran is a polysaccharide typically produced by bacteria growing on a sucrose substrate. Dextran is a polysaccharide comprising a backbone of D-glucose units linked dominantly by alpha-D(1→6) linkages. Depending on the source of dextran, the polysaccharide can have a degree of branching and can have a molecular weight that ranges from about 10,000 to 100,000 and more. Dextran can also be used in the form of derivatives of dextran wherein reactive hydroxyl groups can be modified with various ether such as alkoxy groups including methoxy, ethoxy, etc. or ester groups from a variety of organic acid forming reagents.

The most preferred dextran for use in the barrier layer of the invention comprise low to moderate molecular weight dextrans having a molecular weight in the range of 15,000 to 50,000. Such molecular weights provide an adequate barrier to the transfer of red blood cells into the interior of the reagent zone and promote the most rapid diffusion of the test fluid into the interior of the reaction zone for the rapid visualization of the analyte detection signal.

We have found that many dextran preparations contain significant quantities of low molecular weight monosaccharide, disaccharide, and trisaccharides that can interfere in a variety of the chemistries used in the detection of analytes. Particularly the analysis of test fluids for glucose can be affected by glucose impurities in dextran. Accordingly, the dextran selected for use as the barrier component is typically dialyzed against an aqueous buffer or extracted with alcoholic solvents to remove mono-, di-, etc. saccharide impurities from the dextran material prior to its application to the test strip as a barrier layer.

The dry test strip devices of the invention can use either a chemical assay or an immunoassay reagent system for the detection of the presence of an analyte. The dry test strip can use a dextran having a molecular weight of about 10,000-50,000.

Virtually any analyte detectable using an immunological or chemical assay system can be detected using the dry test strips of the invention. A high molecular weight analyte detected by the device of this invention is characterized as typically large molecule polypeptides, polysaccharides, polynucleic acids, and combinations thereof. Other analytes can include somatic cells, germ cells, bacteria, viruses, and other cellular units. Subcellular units which can be analytes include viral protein, cell wall polysaccharide, DNA, DNA segments, RNA, transfer RNA, messenger RNA, mitochondrial DNA, mitochondria cell nuclei, cell membrane, ribozomes, and other varied cell organelles, subunits and constituent parts. Such large analytes are typically detected using immunological dry test strips of the invention and can have molecular weights in excess of about 50,000. Many such analytes can have a molecular weight ranging from 50,000 to 5,000,000 and more.

The analytical device of the invention can also be used to detect and quantitate the presence of analytes having modest molecular weights, i.e. molecules with a molecular weight less than about 50,000, typically between 5,000 and 50,000. A wide variety of such analytes that comprise natural proteins and protein subunits can be detected using the device of the invention. Such proteins include histones, globulins, nucleoproteins, lipoproteins, glycoproteins, somatotropin, prolactin, insulin, pepsin, human plasma protein constituents including human albumen, thyroxine binding globulin, haptoglobin, ceruloplasmin, cholinesterase, myoglobin, fibrinogen, plasminogen, poly and monoclonal immunoglobulins of the A, D, E, G or M classes, free, light or heavy chains of immunoglobulins, Fab fragment or F(ab')$_2$ fragment, immunoglobulin regions, complement, bloodclotting factors, peptide and protein hormones such as LH, HCG (luteinizing hormone, human chorionic gonadotropin), vasopressin, and others. Such proteins are typically detected using an immunological detection scheme. Antigenic polysaccharides derived from pathogen cell walls also act as an immunological antigen.

Further, small molecules of natural and synthetic origin can also be detected using the dry test strips of the invention. Such small molecules can be detected using both chemical and immunological detection schemes. Such small molecules typically have a molecular weight of about 50 to 5,000, typically about 100 to 2,000. Such analytes include small molecule natural biochemicals, ethical (restricted to sale only on a doctor's prescription) and over the counter and illicit drugs, hormones, peptides, mono and disaccharides, metabolites, pesticides, pollutants and other organic synthetic chemicals. Drugs of interest include ethanol, alkaloids such as morphine, codeine, heroin, dextromethorphan and their derivatives and metabolites. Also included are ergotalkaloids such as LSD lysergicaciddiethylamide, steroid alkaloids, quinoline alkaloids and others. Ethical drugs of interest include steroids, bile acids, digoxin, diethylstilbesterol, ethynylestradiol, and others. Other drugs include barbiturates such as phenobarbitol, secobarbitol, and others. Additionally drugs such as amphetamines, catecholamines, serotonin, L-dopa, epinephrine, chlorpromazine, benzodiazepine, phenothiazine, theophylline, caffeine, cannabis drugs such as cannibinol, tetrahydrocannibinol, vitamins, prostaglandins, antibiotics such as penicillin and the penicillin variants, cephalosporin, and the cephalosporin variants, chloromycetin, actinomycetin, tetracycline. Nucleosides and nucleotides, fragments and derivatives thereof including ATP, NAD, FMN, AZTP azidothymidine, and others can be detected. Additionally, drugs including methadone, meprobamate, Serotonin, lidocain, propanolol, antihistamines, anticolinergic drugs, and others can be detected. Further, analytes typically detected in clinical chemistry analysis including glucose, cholesterol, triglycerides, uric acid, urea, and other typical small molecule chemical analytes can also be determined using the dry test strip devices of the invention.

In the immunochemical assay of the invention, antibodies useful in preparing the dry test strip detection zones of the invention can be prepared in well known polyclonal and monoclonal antibody preparing techniques. Polyclonal antibodies can be raised conventionally in a variety of test animals including mice, rat, rabbit, horse, and others. Monoclonal antibodies can be prepared using well known techniques such as that disclosed by Kohler and Milstein, "Continuous Cultures of Fused Cells Secreting Antibody of Predetermined Specificity", *Nature,* Vol. 256, pp. 495–497, Aug. 7, 1975.

The present invention lends itself to the clinical chemical or at-home detection of analytes in test fluids using oxidant enzymes requiring the presence of atmospheric oxygen to generate a unique signal in the presence of the target analyte. Particularly useful analysis includes detection of glucose using glucose oxidase, the detection of alcohol using alcohol oxidase, and the detection of cholesterol using cholesterol oxidase.

A preferred immunoassay for the detection of analytes that can be used in the dry test strips of the invention is the Liotta type detection system disclosed in Liotta, U.S. Pat. No. 4,446,232. A test strip of the invention comprising a Liotta type device has a matrix of three zones, a first labeled reagent zone, a second trapping zone, and a third detection zone for label detection. The first labeled reagent zone contains a labeled antigen specific antibody or fragment thereof capable of binding the target analyte. The second trapping zone contains bound or immobilized antigen. The third detection zone contains a means for detecting the presence of the label on the antigen specific antibody or fragment thereof. In the operation of the Liotta type device, a test fluid containing the target analyte is applied to the matrix. The analyte in the fluid binds the antigen specific labeled antibody. The presence of the analyte on the binding sites of the antibody causes the analyte-antibody label complex to penetrate the matrix and pass through the trapping zone wherein the presence of the analyte prevents the antibody and its label from becoming trapped by bound antigen. The protected antibody and label penetrate the third zone wherein the presence of the label is detected.

In the absence of analyte in the test fluid, no analyte can bind to the antigen specific labeled antibody. As the application of the test fluid causes the unbound labeled antibody to penetrate the second layer, bound antigen reacts with and traps the labeled antibody in the second layer preventing any of the label from penetrating and causing a detection signal in the third layer. In this way, the presence of analyte in the test fluid can produce a unique quantitative signal in the detection layer.

Detection Zone Substrate Materials

The primary function of the materials making up the detection zone is to act as a site or locus for an effective concentration of the detection zone materials and to provide an effective flow of the test fluid through the zone to permit reaction between the analyte and either the immunoassay or chemical assay reagents contained within the test device. The detection zone can be of a variety of shapes and forms having varied dimensions. The typical zone material will have a thickness of at least 0.1 mil (1 mil=0.001 inches), typically greater than 1 mil, generally in the range of 10 to 30 mil. Such substrates can be semi-opaque, translucent or transparent. However, the signal generated by the immuno or chemical assay should not be masked by the nature of the support. A variety of organic and inorganic polymers, both natural and synthetic may be employed in the formation of the detection zone including polyethylene, polyvinyl chloride, polypropylene, poly-4-methyl butene, polystyrene, polymethacrylate, polyethylene terephthalate polyester, rayon, nylon, polyvinyl butyrate, silicone films, cellulose, cellulose acetate, nitrocellulose, etc. and others. Other materials which may be considered include paper, glass, fiberglass, ceramics, metals, metal foils, metalloids, semi-conductive materials, and others. Additionally, natural substances that can form gels or films including proteins, protein derivatives, cellulosics, drying oils, and others can be implemented.

A preferred substrate for forming the reagent zone matrixes of the invention comprise a porous nylon substrate formed by casting a porous nylon sheet on a nonwoven substrate layer. Such a layer provides uniform pore size (minimum of 0.04 micron, preferably 0.2 to 1 micron chemical inertness to typical solvents and reagents used in forming the dry test strips, and provides significant mechanical strength and integrity that promote rapid and accurate production. The dry test strip device can take the form of a long strip of paper that can be placed in a reel dispenser from which short segments can be removed. The short segments can be easily handled and to the segments can be applied a test fluid. The use of the dry test strip format described here is similar to that involving the use of a pH paper.

Additionally, the dry test strip devices of this invention can be used in a number of formats wherein the dry test strip detection zones are carried by or held within mechanical support structures. The minimal device of the supported detection zone aspect of the invention involves a detection zone adhered to a carrier strip support.

The carrier strip of the invention that bears the reagent zone and the barrier layer typically comprises a synthetic organic polymer having sufficient strength and flexibility to survive manufacture and use. Preferred polymeric carrier strips are made from transparent or semitransparent polymers such as polystyrene, polyethylene terephthalate, polyester, and others.

Preferably the carrier strip used in preparing the detection device of the invention using a detection system requiring the presence of atmospheric oxygen, has a construction that promotes the transfer of oxygen from the atmosphere to the reaction site. The dry test strip can be formed in such a way to promote atmospheric contact. One means comprises forming an aperture in the carrier strip at the contact zone between the strip and the detection zone. Such aperture can take the form of an oval, circular, polygonal shaped cut-out in the carrier strip. Alternatively, the detection zone can be attached to the carrier strip using a construction design permitting the flow of atmospheric oxygen into the interface between the detection zone and the carrier strip. Such oxygen flow to the interface can be promoted by providing attachment means between the detection zone and the carrier strip such that a significant area volume between the detection zone and the carrier strip remains unoccupied providing access to atmospheric oxygen. Such a construction can be obtained by adhering the detection zone to raised adhesive areas or to small areas of double-sided adhesive tape leaving the majority of the reverse side of the detection zone to the contact of atmospheric oxygen. Alternatively, the aperture can comprise a highly oxygen permeable polymeric layer introduced into the carrier strip layer in intimate contact with the color forming zone, through which oxygen can readily be transported for reaction. Such aperture typically is located on the carrier strip opposite the reagent zone for rapid transfer of atmospheric oxygen into the reagent zone. Preferably the dimensions of the aperture approximate the dimensions of the reagent zone and are preferably smaller than the reagent zone but expose a significant portion of the area of the reagent zone for oxygen transferred visual detection of the color change.

In certain aspects of dry test strip analysis, a detection zone can be held on a carrier strip in conjunction with other zones. One embodiment of such a multi-zone detection system is a device manufactured through the teachings of Liotta, referenced above. In such a multi-zone device, the polysaccharide barrier material can be used in a discrete layer protecting each zone, protecting a single zone, or can be dispersed throughout one or more of the zones in the invention. In one embodiment, an amount of the protection barrier material can be dispersed through each zone thus increasing the rate of penetration of the test fluid while providing RBC sequestration or segregation protecting the detection zone from RBC interference. Other multi-zone detection devices are known in the art and the device of the invention is not limited by this disclosure to the Liotta technology.

The dry test strips of the invention are preferably manufactured by forming the detection zone by introducing the reagent system into an appropriate substrate material. The substrate material is then coated or impregnated with the polysaccharide barrier layer, either before, during or after incorporating the reagent zone onto the carrier strip. Preferably the aperture in the carrier strip is formed before the detection layer is applied to the carrier strip.

We have found that often the reagent systems used in detecting the analytes must be applied to the substrate layer in two steps. The components of the reagent systems are typically aqueous soluble. As a result, in a second contact between an aqueous solution containing various components of the reagent system, the aqueous reagent system contained in the substrate material can leach from the substrate, reagent system components. Accordingly, in a second contact between a liquid containing reagent components, the second reagent is made up in a solvent in which the components contained by the reagent zone are insoluble. We have found, for example, that many components of the reagent zone such as enzymes and water soluble polymers can be applied to the reagent zone in an aqueous solution, while other components of the reagent system which are soluble in methanol can be applied in a second step from methanol solution without leaching useful components from the substrate.

The polysaccharide barrier layer is added to or coated on the substrate. The substrate can contain a preformed reagent system, or the detection reagent system can be added after the barrier layer is formed. The polysaccharide material is contacted with the substrate material and can either form a discrete barrier over the substrate material or can be uniformly dispersed throughout the substrate material. Since the generation of a chemical signal is typically viewed from the side of the substrate opposite that of sample application, red blood cell exclusion by the polysaccharide barrier layer can occur through the substrate as long as few red blood cells reach the opposite end of the substrate layer. The polysaccharide material can be applied to the substrate material in the form of the solution or a suspension of the polysaccharide material in a suitable carrier medium. Preferred carrier mediums include liquid solvents compatible with the substrate materials and other components used in the dry test strip of the invention. Most preferred carrier mediums comprise aqueous mediums such as known buffer solutions useful in preparing biologically useful materials. The polysaccharide material can be added to the substrate layer in a solution or a suspension where the polysaccharide material is the sole component. However, other water soluble materials can be added with the dextran material to the substrate layer including chelating agents, water soluble polymers, antioxidants, dyes, enzymes, coenzymes, and other materials.

We have found that in order to achieve the maximum red blood cell exclusion from the reagent zone, that the concentration of the polysaccharide material in aqueous medium in preparation of the test strip is important. We have found that maintaining the concentration of the dextran polysaccharide material in a range of about 7 to 40 wt-% of the polysaccharide material based on the aqueous composition provides the highest red blood cell exclusion while maintaining rapid test fluid diffusion through the test device for rapid analyte detection. Most preferably the concentration of the polysaccharide material or the preferred dextran red blood cell exclusion material comprises a concentration of about 10 to 35 wt-% of dextran in the aqueous medium, and most preferably for reasons of ease of preparation, rapidity of color development, and economy, a dextran having a molecular weight of from about 10,000 to 40,000 is used at a concentration of about 15 to 25 wt-% in the aqueous buffered solution.

DETAILED DISCUSSION OF THE DRAWINGS

Figure 1:
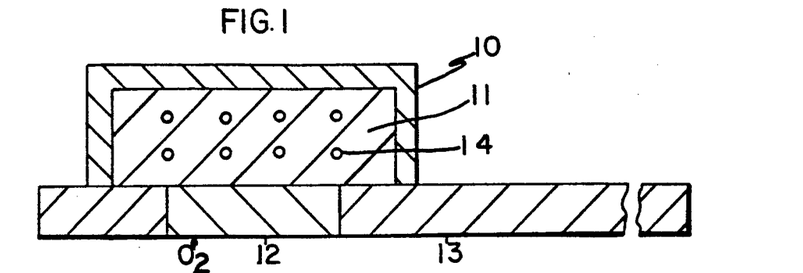
FIG. 1 is a cross-sectional drawing of a chemical assay dry test device of the invention showing an integral barrier layer covering a reagent zone on a test strip having a color change visualization aperture that can act as an oxygen window.

FIG. 1 is a cross-sectional view of a dry test strip of the invention. The dry test strip comprises a carrier strip 13 having an aperture 12 in the carrier strip permitting the rapid access to the chemical detection system 14 within the substrate layer 11 for atmospheric oxygen. The detection system 14 can often use enzymes that require the presence of atmospheric oxygen to generate peroxide which is a driving force in the detection system. The substrate 11 containing the detection system 14 is enclosed by a barrier layer 10 comprising the polysaccharide materials of the invention. A discrete barrier layer is shown in FIG. 1 surrounding and enclosing entirely the detection substrate material preventing intrusion of red blood cells.

Figure 2:
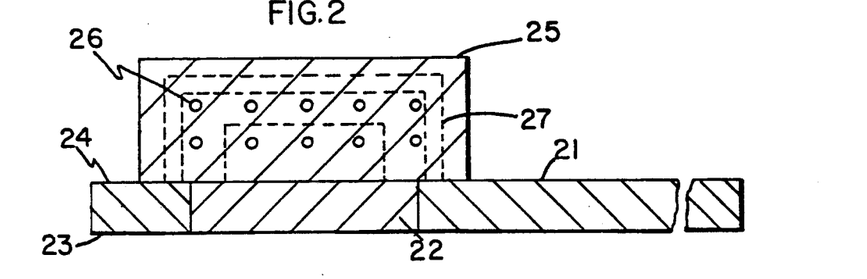
FIG. 2 shows a similar chemical assay dry test strip which uses a highly permeable plastic layer as a visualization aperture and oxygen window.

FIG. 2 is a cross-sectional view of a dry test strip of the invention. Carrier strip 21 is equipped with an aperture 22 comprising an oxygen permeable material that can be used in the instance that the indicator or detection zone material must be protected from the atmosphere. The carrier strip 21 has an aperture side 23 and a detection zone side 24. On the detection zone side 24 covering the aperture zone 22 is the detection zone substrate material 25. The detection zone material contains the reagent detection system 26 and is impregnated uniformly throughout the detection zone with the polysaccharide exclusion barrier material 27.

Figure 3:
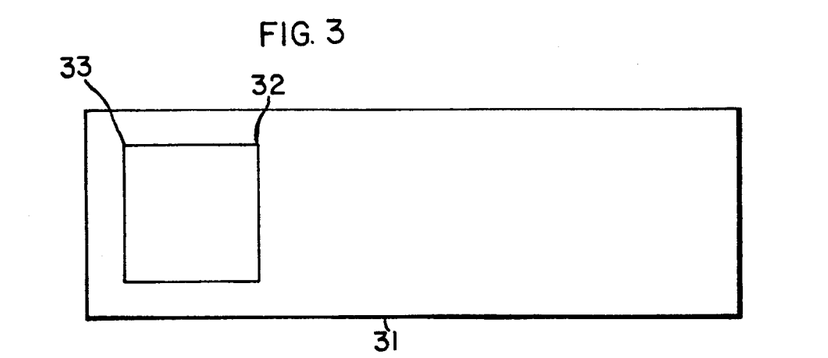
FIGS. 3 and 4 are cross-sectional views of an immunoassay dry test strip showing a barrial layer over a matrix having three zones that contain immunoassay reagents useful for detecting the presence of an analyte immunologically and providing a detectable signal. The dry test strips utilize a visualization aperture or window that can serve as a source of oxygen for the detection system or a highly permeable clear plastic film as the visualization aperture.

FIG. 3 is a planar view of the detection zone side of the dry test strip of the invention. Carrier strip 31 is shown bearing the detection zone substrate material 32 wherein the barrier polysaccharide material 33 is uniformly distributed.

Figure 4:
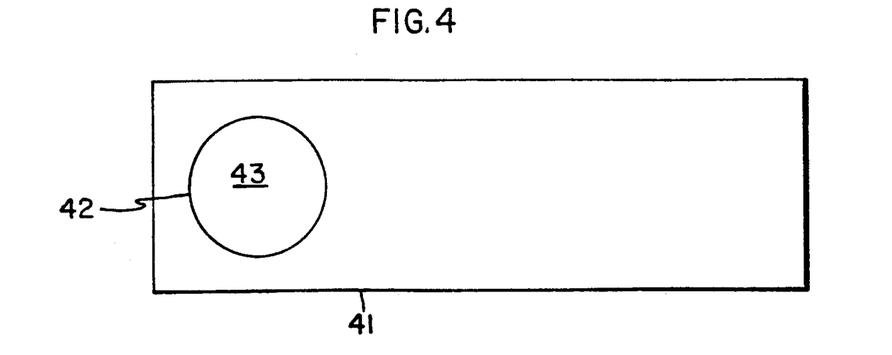

FIG. 4 is a planar view of the aperture side of the dry test strip of the invention. The carrier strip 41 is shown with the aperture 42 containing the oxygen permeable material 43 that permits the flow of atmospheric oxygen into the detection zone.

Figure 5:
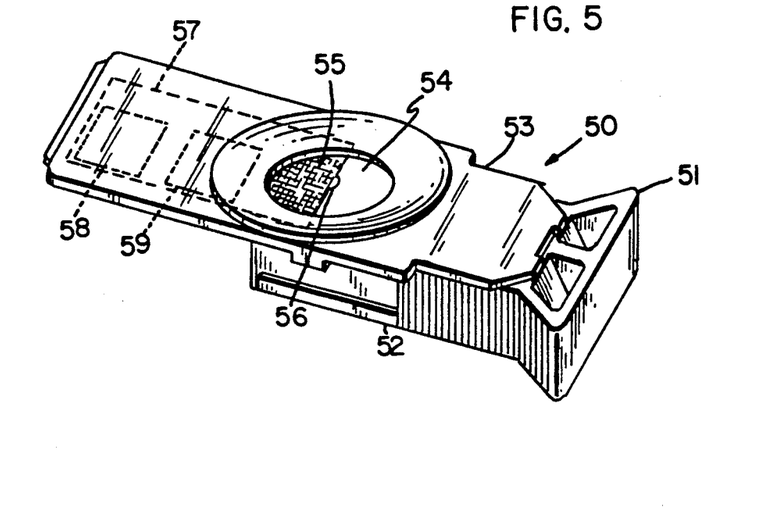
FIG. 5 is an isometric view of an instrumentally read device 50 that comprises a lance that can simultaneously lances a body part such as a finger pad to obtain a blood sample, distributes the blood sample through a wick to a detection zone and a wetting or reference zone, permits the detection reaction to occur which can be read from the exposed detection means.

FIG. 5 is a view of a plastic machine read holder for the detection strips of the invention. The holder 50 comprises a handle 51 and a body 52 supporting a circular touch zone 53 having an internal opening 54. Exposed within the opening 54 is a wicking fabric 55 and a lance 56. The wicking fabric 55 is in fluid contact with the hidden dry test strip 57. The dry test strip 57 comprises a registration zone 58 and a detection zone 59. As the registration zone 58 is wetted by the test fluid, typically blood, the wetting of the registration zone 58 shows that full wetting has occurred. The detection zone 59 generates a color or other signal specifically indicating the concentration of the target analyte present in the blood serum.

Figure 6:
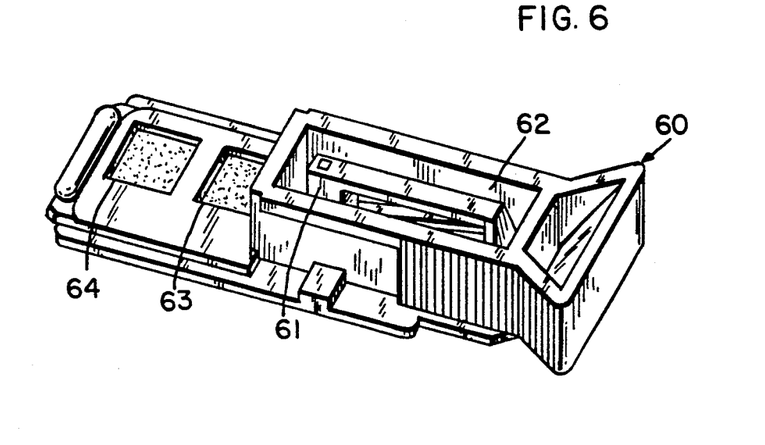
FIG. 6 is an isometric view of the opposite side of the device of FIG. 5 showing the lance means and a window for both the wetting or reference zone and the detection zone.

FIG. 6 is a view of the opposite side of the holder of FIG. 5. The holder 60 contains a lance 61 mounted on a flexible support 62. In use the flexible support 62 is flexed, causing the lance 61 to penetrate through the surface of the holder, entering a finger to provide a blood sample. The holder 60 further comprises windows 63 and 64 which show a signal in the presence of the target analyte and the successful wetting of the dry test strip with the test fluid.

Figure 7:
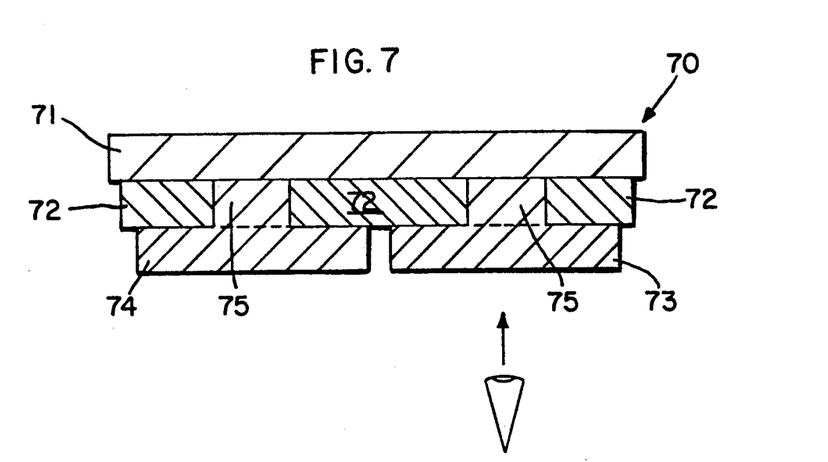
FIG. 7 shows a cross-sectional view of an immunoassay dry test strip showing a barrier layer supporting adhesive attachment means holding a detection zone in inherent contact to the carrier strip.

FIG. 7 shows a preferred embodiment of the dry test strip of the invention adapted for the holder of FIGS. 5 and 6. The dry test strip 70 comprises a fabric wicking layer 71 to which is attached adhesive means 72 holding the detection zone 73 and the registration zone 74 to the wicking fabric 71. Formed between the adhesive means 72 are windows 75 which permit the flow of test fluid from the wicking fabric 71 to the registration zone 74 or the detection zone 73. The test is read from the side opposite that of the wicking fabric.

The dry test strips of the invention can be used for the detection of analytes in a variety of test fluids containing red blood cells including whole blood, whole blood derivatives, red blood cell suspensions, red blood cell preparations, urine, cerebral spinal fluid, ascites, saliva, or any other clinically important fluid containing significant numbers of red blood cells. In use, controlled volume of the test fluid is applied to the barrier side of the dry test strip of the invention. Typically useful volumes range from about 5 to 500 microliters, preferably 5 to 100 microliters, most preferably about 10 to 50 microliters. The test fluid can be applied to the dry test strip using any suitable volumetric measuring device. The test fluid is permitted to diffuse through the detection zone of the dry test strip and needs no blotting or wiping. However blotting or wiping can be used when necessary for aesthetic or other reasons. The detection signal is typically read from the side of the dry test strip opposite that of the detection zone through the aperture in the carrier. A visual color change can be read visually by an operator to obtain both qualitative, semi-quantitative and quantitative results using comparison charts. The visual or other detection means can be read and quantitated by a machine on a manual or semi-automated basis. Typically fluorescence can be measured in well characterized values, while visual color changes can be read by reflectance.

EXAMPLE I

A dry test strip of the invention was prepared by first preparing a methanol solution containing, in each 20 milliliters of the solution, 200 milligrams of orthotolidine. In addition an aqueous citrate-EDTA buffer solution at pH of 6 was prepared containing 6,000 units of glucose oxidase, 9,000 units of horseradish peroxidase, 0.5 wt-% of sodium dodecyl sulfonate, 20 wt-% of an 80,000 molecular weight dextran, 0.8 wt-% of a vinyl ether/maleic anhydride copolymer, 0.4 wt-% of a polyvinylpyrollidone polymer having a molecular weight of 40,000, 0.005 wt-% of ascorbic acid, and 0.75 wt-% of tartrazine (FD&C yellow dye No. 5). The dextran used in this Example was dialyzed against the for 5 days, replacing the buffer once per day to remove mono, di and trisaccharide impurities. A nylon membrane prepared by casting nylon on a nonwoven polyfabric (ULTIPOR 66, Pall) was first dipped in the citrate EDTA buffer solution, scraped, dried for 4 minutes at 75° C., dipped in the methanolic orthotolidine solution, scraped and dried for 2 minutes at 75° C. After removal of the methanolic medium, the membrane was cut into a detection zone of dimensions approximately 6 by 6 millimeters, and applied to a carrier strip having dimensions of 0.25 by 3 inches containing an aperture in the carrier strip having a diameter of 5/32 inch.

EXAMPLE II

Example I was repeated exactly except that a dextran having a molecular weight of 35,600 was used.

EXAMPLE III

Example I was repeated exactly except that a dextran having a molecular weight of 17,200 was used.

EXAMPLES IV-VI

Examples I–III were repeated except that 0.6 K units of glucose oxidase and 0.9 K units of horseradish peroxidase were substituted for the 6 K units and 9 K units of glucose oxidase and horseradish peroxidase, respectively.

DISCUSSION

Each of the test strips prepared in the Examples I–VI provided acceptable performance, while the test strip of Examples II and III provided a complete end point reading at about 1 minute and about 45 seconds after application of 15 microliters of whole blood.

EXAMPLE VII

A dry test strip of the invention was made using the following procedure. A methanolic solution was prepared containing in each 10 milliliters of methanol, 50 milligrams of orthotolidine, 10 milligrams of 3,3',5,5'-tetramethyl benzidine, 0.25 wt-% sodium dodecyl sulfonate, 0.5 wt-% of a methyl vinyl ether/maleic anhydride copolymer. Additionally an aqueous citrate EDTA buffer having a pH of about 6 was prepared containing, per each 10 milliliters of buffer, 6 K units of glucose oxidase and 9 K units of peroxidase. The citrate EDTA buffer contained 20 wt-% of a 40,000 molecular weight dextran, 0.8 wt-% of the methyl vinyl ether/maleic anhydride copolymer, 0.4 wt-% of a polyvinylpyrollidone polymer having a molecular weight of 40,000, 0.005 wt-% of ascorbic acid, and 0.075 wt-% of tartrazine. Nylon membranes were first dipped into the citrate-EDTA buffer enzyme solution, removed, scraped, dried for 4 minutes at 75° C., and then dipped in the methanolic reagent solution, withdrawn and dried for 2 minutes at 75° C. The nylon membrane was then divided into detection zone portions having dimensions of 6 by 6 millimeters, and applied to a plastic carrier strip over an aperture having a diameter of 5/32 inch.

EXAMPLE VIII

Example VII was repeated exactly except that the methanol dip solution contained 0.1 wt-% sodium dodecyl sulfonate and 0.2 wt-% of the methyl vinyl ether/maleic anhydride copolymer.

EXAMPLE IX

Example VII was repeated exactly except that the methanol dip contained 0.1 wt-% of the sodium dodecyl sulfonate.

DISCUSSION

The dry test strips of the invention prepared in Examples VII through IX were tested by applying 20 microliters of whole blood containing in each application 20, 40, 80, 120, 160, 250 and 465 milligrams of glucose per each 100 milliliters of blood. In each evaluation, no red blood cell penetration was noted. The color signal was smooth and had no local concentrations. The optimum color signal was obtained in Example VII, while the colors in Examples VIII and IX appeared dark but could be discriminated at even the highest concentrations of glucose.

The foregoing detailed description of the invention is provided to illustrate and explain the invention's dry test strip and to explain and illustrate its manufacture and use. While many embodiments of the invention can be made without departing from the spirit and scope of the invention, the invention resides in the claims hereinafter appended.

We claim:

1. A dry test strip for detection of an analyte in a test fluid comprising:
   (a) a porous detection zone having a test fluid application site physically separate from a visualization site containing a signal generating system that produces a signal in the presence of the analyte, wherein the detection zone pores are about 0.04 to 1 micron; and
   (b) dextran, having a molecular weight of about 10,000 to 50,000 dispersed in the detection zone at a concentration effective to prevent penetration of red blood cells through the detection zone to the visualization site;

wherein any red blood cells present in the test fluid interact with the dextran adjacent the test fluid application site to prevent their penetration through the detection zone to the visualization site thereby essentially eliminating red blood cell interference with the signal generation.

2. The dry test strip of claim 1 wherein the dextran comprises a polymer of D-glucose having $\alpha D-(1\rightarrow 6)$ linkages.

3. The dry test strip of claim 1 wherein the signal generating system contained within the detection zone comprises a chemical assay.

4. The dry test strip of claim 3 wherein the chemical assay comprises a glucose assay reagent.

5. The dry test strip of claim 3 wherein the chemical assay comprises a cholesterol assay reagent.

6. The dry test strip of claim 1 wherein the signal generating system in the detection zone comprises an immunoassay.

7. The dry test strip of claim 6 wherein the detection zone comprises a first labeled reagent zone containing a labeled antibody or fragment thereof specific for the analyte, a second trapping zone comprising immobilized antigen which specifically binds unbound labeled antibody or fragment thereof, and a third signal generation zone containing means to detect the presence of the label.

8. The dry test strip of claim 1 wherein the detection zone is adhered to a polymeric carrier strip.

9. A dry test strip for detection of an analyte, in a test fluid containing red blood cells which comprises a carrier strip having a porous detection zone having pores of about 0.04 to 1 micron and containing a signal generating system that produces a signal in the presence of the analyte, said detection zone having a discrete barrier layer on the surface of the detection zone comprising a sufficient amount of dextran having a molecular weight of about 10,000 to 50,000 to prevent the penetration through the porous detection zone and interference with the signal generation system by the red blood cells.

10. The dry test strip of claim 9 wherein the dextran comprises a polymer of D-glucose having $\alpha D-(1\rightarrow 6)$ linkages.

11. The dry test strip of claim 9 wherein the signal generating system contained in the detection zone comprises a chemical assay.

12. The dry test strip of claim 9 wherein the signal generating system in the detection zone comprises an immunoassay.

13. The dry test strip of claim 12 wherein the detection zone comprises a first labeled reagent zone containing a labeled antibody or fragment thereof specific for the analyte, a second trapping zone comprising immobilized antigen which specifically binds unbound labeled antibody or fragment thereof, and a third single generation zone containing means to detect the presence of the label.

14. A method for detecting an analyte in a test fluid which method comprises:
(a) applying the test fluid to a dry test strip comprising
a porous detection zone having pores of about 0.04 to 1 micron and a test fluid application site physically separate from a visualization site containing:
(i) a signal generating system that produces a signal in the presence of the analyte; and
(ii) dextran having a molecular weight of about 10,000 to 50,000, dispersed through the detection zone at a concentration effective to prevent penetration of any red blood cells present in the fluid through the detection zone; and
(b) detecting the concentration of the analyte; wherein any red blood cells present in the test fluid interact with the dextran adjacent the application site to prevent their penetration through the detection zone to the visualization site thereby essentially eliminating red blood cell interference with the signal generation.

15. The method of claim 14 wherein the dextran comprises a polymer a D-glucose having $\alpha D-(1\rightarrow 6)$ linkages.

16. The method of claim 14 wherein the signal generating system contained within the detection zone comprises a chemical assay.

17. The method of claim 14 wherein the signal generating system in the detection zone comprises an immunoassay.

18. The method of claim 17 wherein the detection zone comprises a first labeled reagent zone containing a labeled antibody or fragment thereof specific for the analyte, a second trapping zone comprising immobilized antigen which specifically binds unbound labeled antibody or fragment thereof, and a third single generation zone containing means to detect the presence of the antibody label.

19. The method of claim 14 wherein the test fluid is selected from the group consisting of serum, plasma, urine, cerebral spinal fluid, ascites, and saliva.

20. The method of claim 14 wherein the test fluid comprises whole blood, a red blood cell containing fraction thereof or a red blood cellular suspension in a compatible diluent.

21. The method of claim 14 wherein the detection zone is adhered to a polymeric carrier strip.

* * * * *

UNITED STATES PATENT AND TRADEMARK OFFICE
CERTIFICATE OF CORRECTION

PATENT NO.   :   5,212,060
DATED        :   May 18, 1993
INVENTOR(S)  :   Catherine B. Maddox It is certified that error appears in the above-identified patent and that said Letters Patent is hereby corrected as shown below:

On title page, line (63), "88,454" should read --18,454-- .

In Column 13, line 19, after the word "the", insert --test-- .

Signed and Sealed this

Fifth Day of April, 1994

Attest:

*Attesting Officer*

BRUCE LEHMAN
*Commissioner of Patents and Trademarks*